United States Patent [19]

Wedeen et al.

[11] Patent Number: 4,625,169
[45] Date of Patent: Nov. 25, 1986

[54] FLOW IMAGING BY MEANS OF NUCLEAR MAGNETIC RESONANCE

[75] Inventors: Van J. Wedeen; Bruce R. Rosen, both of Cambridge, Mass.

[73] Assignee: The General Hospital Corporation, Boston, Mass.

[21] Appl. No.: 640,040

[22] Filed: Aug. 10, 1984

[51] Int. Cl.[4] .............................................. G01R 33/20
[52] U.S. Cl. .................................... 324/309; 324/307
[58] Field of Search ............... 324/300, 306, 307, 309, 324/312, 313, 314, 318, 322; 128/653

[56] References Cited

U.S. PATENT DOCUMENTS

| 3,562,632 | 2/1971 | Kirkland | 324/306 |
|---|---|---|---|
| 4,110,680 | 8/1978 | Bergmann et al. | 324/306 |
| 4,442,404 | 4/1984 | Bergmann | 324/309 |
| 4,516,075 | 5/1985 | Moran | 324/309 |
| 4,516,582 | 5/1985 | Redington | 324/309 |
| 4,523,596 | 6/1985 | Macovski | 324/309 |
| 4,528,985 | 7/1985 | Macovski | 324/309 |
| 4,532,473 | 7/1985 | Wehrli | 324/309 |

OTHER PUBLICATIONS

Moran, "A Flow Velocity Zeugmatographic Interlace For NMR Imaging in Humans", Magnetic Resonance Imaging, vol. I, pp. 197–203.
Macovski, "Selective Projection Imaging: Applications to Radiography and NMR," IEEE Transactions on Medical Imaging, vol. ML-1, No. 1, Jul., 1982, pp. 42–47.
Hahn, "Detection of Sea-Water Motion by Nuclear Precession", Journal of Geophysical Research, vol. 65, No. 2, pp. 776–777.
van Dijk, "Direct Cardiac NMR Imaging of Heart Wall and Blood Flow Velocity", Journal of Computer Assisted Tomography, 8(3), pp. 429–436, Jun., 1984.
Mills et al., "Nuclear Magnetic Resonance: Principles of Blood Flow Imaging", American Journal of Neurology, Nov./Dec., 1983, pp. 1161–1166.
Singer, "NMR Diffusion and Flow Measurements and an Introduction to Spin Phase Graphing", Journal of Physics E Scientific Instruments, Apr., 1978, vol. 11, No. 4, pp. 281–376.
Singer et al., "Nuclear Magnetic Resonance Blood Flow Measurements in the Human Brain", Science, Aug., 1983, vol. 221, No. 4610, pp. 654–656.

Primary Examiner—Michael J. Tokar

[57] ABSTRACT

Nuclear magnetic resonance apparatus for forming an image representative of a velocity profile of a fluid flowing in a vessel in which the fluid is stimulated to produce a time-dependent magnetic resonance signal, Fourier-transformed data is derived from the time-dependent magnetic resonance signal, the stimulating is done so as to introduce, into a predetermined component of the Fourier-transformed data, spatially-dependent phase information indicative of the velocity profile of the fluid, and the predetermined component is extracted for display as the image representative of the velocity profile.

32 Claims, 16 Drawing Figures

FLOW IMAGING BY MEANS OF NUCLEAR MAGNETIC RESONANCE

BACKGROUND OF THE INVENTION

This invention relates to nuclear magnetic resonance (NMR) imaging.

NMR imaging techniques can be used to form a picture of a cross-section of three-dimensional objects (for example, human organs) in which their structure is indicated by variations in intensity or color of the picture.

One common technique for forming such an image uses a first magnetic field pulse having a linear gradient along a z-axis ($G_z$) to select the "slice" corresponding to the desired cross-section, a second pulse (called a phase-encoding pulse) having a linear gradient along the y-axis ($G_y$) to encode nuclei at different y-axis positions with different precessional phases, and a third linear gradient pulse (called a frequency-encoding pulse) along the x-axis ($G_x$) to encode nuclei at different x-axis positions with different frequencies. An appropriately modulated RF signal generator imposes a 90° RF pulse followed (after an appropriate interval) by a 180° pulse. The resulting time-dependent resonance spin-echo signal is measured and stored. The process is repeated to obtain a family of spin-echo signals each based upon a different magnitude of phase-encoding gradient $G_y$. The family represents a two-dimensional array of time-dependent information. A two-dimensional Fourier transformation of the spin-echo signal array produces a two-dimensional array of frequency-domain data which can be displayed as an image of the selected slice.

In addition to such images of the structure of organs, it has been suggested that NMR techniques be used in analyzing flow characteristics. For example, information about the flow of blood in an artery could be useful in analyzing deformities of the wall of the artery.

Moran, "A Flow Velocity Zeugmatographic Interlace for NMR Imaging in Humans", Magnetic Resonance Imaging, 1983, discloses adding to the usual imaging gradients, a special sequence of gradient pulses (for example, along the z-axis) to encode the nuclei with information about their velocity which can then be recaptured by Fourier transformation. The special gradient pulses are arranged to eliminate any dependence of the velocity-encoded information on spatial location. The article suggests using the imaginary component of the resulting data as an image of flow-current-density, and the ratios of the real to imaginary components of the data as an image of specific-flow-density.

In addition to cross-sectional images, NMR techniques have been used to produce three-dimensional projection images in which the data for a stack of cross-sectional slices are effectively added together. Macovski, "Selective Projective Imaging: Applications to Radiography and NMR," IEEE Transactions on Medical Imaging, July, 1972, discloses selective projective imaging in which subtraction of unwanted image components is proposed to be used in displaying moving blood without displaying the surrounding tissue.

Hahn, E. L., J. Geophys. Res. 65, 1960, p. 776, recognized that the motion of nuclei in a magnetic gradient will modify their phases in a way which is reflected in a shift in phase at the center of the spin echo.

SUMMARY OF THE INVENTION

In general, the invention features forming an image representative of a velocity profile of a fluid flowing in a vessel by stimulating the fluid to produce a time-dependent magnetic resonance signal, producing Fourier-transformed data from the time-dependent resonance signal, the stimulating being done so as to introduce, into a predetermined component of the Fourier-transformed data, spatially-dependent phase information indicative of the velocity profile, and extracting the predetermined component for display as the image representative of the velocity profile.

In preferred embodiments, the phase information includes phase values for an array of positions in the fluid, the image comprises an array of display points each characterized by a visual parameter (e.g., intensity) whose magnitude represents the phase value for a corresponding position in the fluid, and phase offset amounts are imposed on the phase values to impart a visible pattern (e.g., parallel, evenly spaced stripes) to the velocity information in the image; the phase offset amounts increase linearly with distance along a predetermined direction in the fluid, and the stripes are spaced along one dimension of the image corresponding to the predetermined direction; and the Fourier transformation is calculated from a selected time segment of the time-dependent resonance signal (e.g., a spin-echo signal), and the selected time segment is off-center with respect to the center time point of the resonance signal.

Also in preferred embodiments, a first magnetic gradient pulse is imposed along one direction introducing phase information indicative of velocity of the fluid along the one direction, and a second magnetic gradient pulse is imposed along a second direction (e.g., perpendicular to the one direction), the durations of the pulses are regulated so that the first magnetic gradient pulse is longer (e.g., at least five times longer) than the second magnetic gradient pulse to cause velocity of the fluid along the one direction to have greater influence on the image than velocity of the fluid along the second direction; the vessel is oriented with the predominant direction of flow aligned with the one direction; the first pulse is imposed immediately after the second pulse to reduce the effect on the image of velocity of the fluid along the second direction; and the predetermined component is the real component of said Fourier-transformed data.

Also in preferred embodiments, projection images are produced of a vessel which is part of a larger specimen, the specimen includes stationary portions, the Fourier-transformed data includes a component which carries phase information derived from the stationary portions, and a component is derived from the Fourier-transformed data for display which reduces the effect of the stationary portions on the image; and the component for display is 90° out of phase from the component which carries the phase information from the stationary portions.

The velocity profile images are easily obtained without requiring special velocity-encoding gradient pulses in addition to the phase-encoding and frequency-encoding pulses, and without requiring special processing of the spin-echo signals. The images are produce from the readily available real component of the Fourier-transformed data. For embodiments in which there is an additional background phase offset, the images are in the form of stripes across the vessels which are easy to read both conceptually and for the purpose of actual velocity measurements. For embodiments in which a projection image is formed, the selection of a display component 90° out of phase from the predominant stationary fluid component, makes it easier to see the effects of the moving fluid. Triggering the frequency-encoding gradient immediately after the phase-encoding gradient reduces the effect of motion which might otherwise occur between the two pulses. Arranging the pulses to produce a high ratio of phase shift to velocity enables good resolution of velocity. Aligning the axis of motion with the axis of the frequency-encoding pulse and making the frequency-encoding pulse longer than the phase-encoding pulse enhances sensitivity to the velocity components of particular interest.

Other advantages and features of the invention will become apparent from the following description of the preferred embodiment, and from the claims.

DESCRIPTION OF THE PREFERRED EMBODIMENT

We first briefly describe the drawings.

DRAWINGS

STRUCTURE

Figure 1:
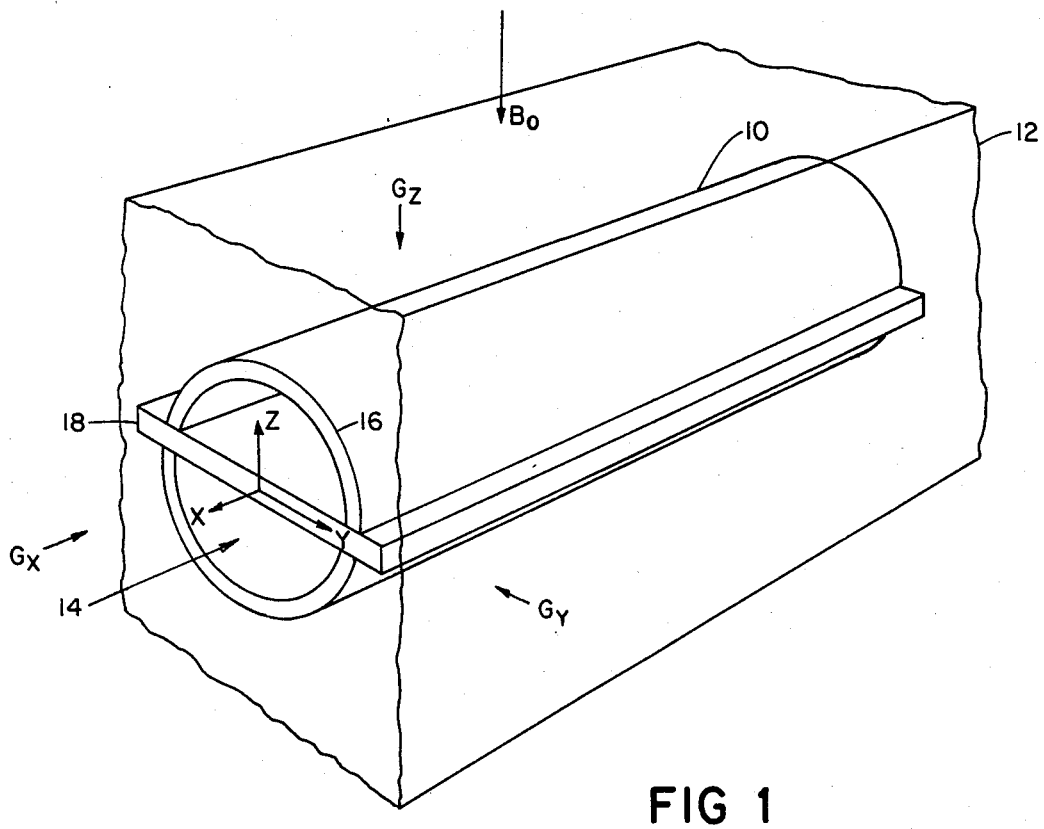
FIG. 1 is an isometric view of a short segment of a blood vessel and surrounding tissue.

Referring to FIG. 1, blood vessel 10 lies within a matrix of tissue 12 and carries blood flowing in the direction indicated by arrow 14. The velocity of the blood in direction 14 tends to vary depending on how close it is to wall 16 of vessel 10. For example, in certain types of laminar flow the velocity of the blood is smallest at wall 16 and increases to a maximum at the central axis x of vessel 10. Thus, for a particular imaginary planar slice 18 (having a particular location along axis z) the blood velocity component in the x direction might vary from small to large to small as one traverses the slice from one wall to the opposite wall in a direction indicated by axis y.

Figure 2:
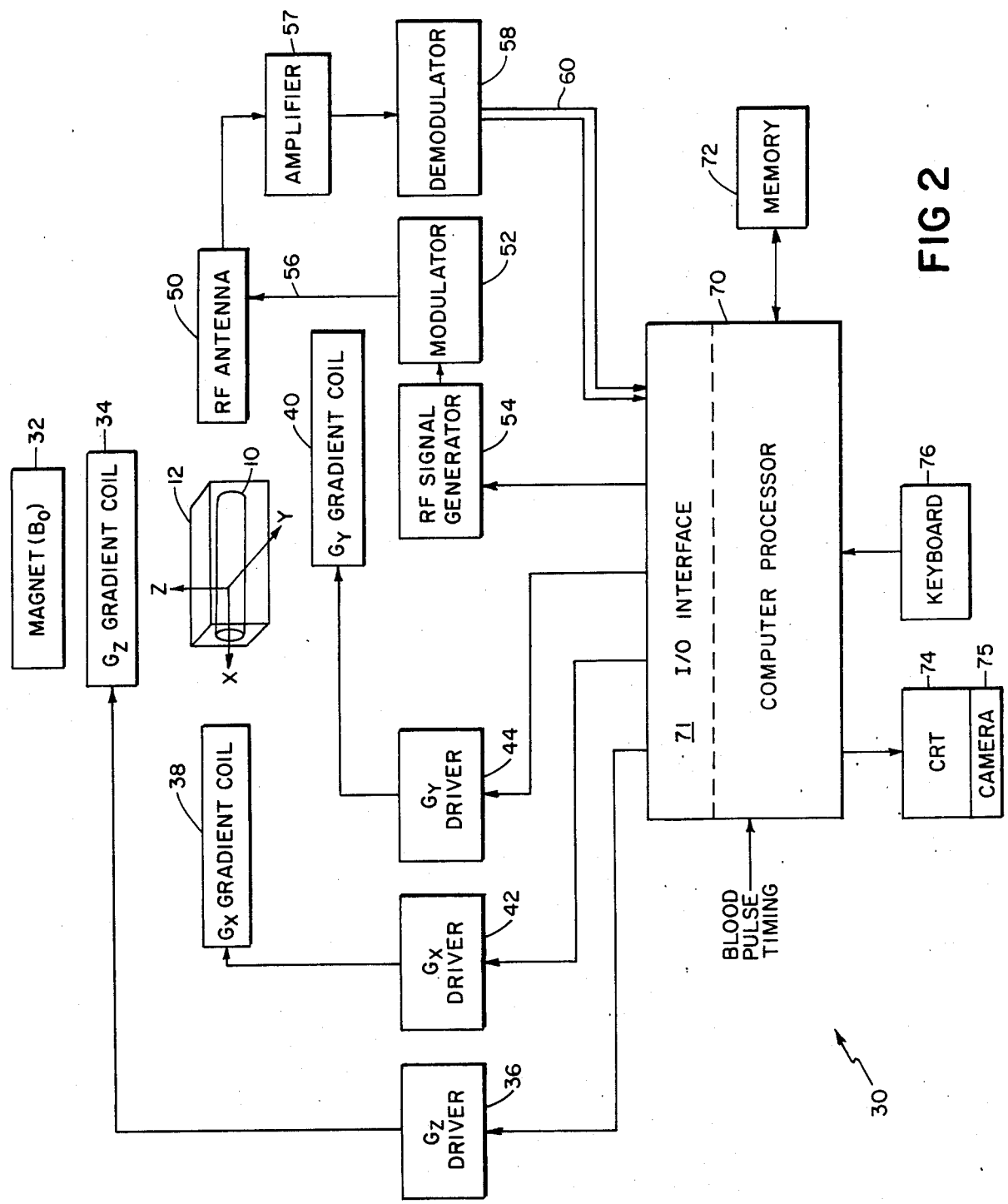
FIG. 2 is a block diagram of NMR apparatus.

Referring to FIG. 2, nuclear magnetic resonance apparatus 30 has a magnet 32 for imposing a uniform constant magnetic field $B_0$ on vessel 10 and tissue 12. A $G_z$ gradient coil 34 (arranged to provide a linear magnetic field gradient along the z-axis) is connected to a $G_z$ driver 36, which can provide selected levels of power at selected times to coil 34. Likewise, $G_x$ gradient coil 38 and $G_y$ gradient coil 40, which can provide linear magnetic field gradients respectively along the x-axis and y-axis, are respectively connected to $G_x$ driver 42 and $G_y$ driver 44, for providing power to the coils.

An RF antenna 50 (arranged to transmit and receive an RF signal to and from blood vessel 10 and tissue 12) is connected to modulator 52 which is in turn connected to an RF signal generator 54 and is arranged to impose an RF signal at a selected frequency and at selected times upon vessel 10 and tissue 12. RF antenna 50 is also connected via amplifier 57 to demodulator 58, which is arranged to demodulate received signals (from vessel 10 and tissue 12) into quadrature real and imaginary components (indicated by the doubling of line 60).

Computer processor 70 is connected via I/O interface 71 to $G_x$, $G_y$, and $G_z$ drivers 42, 44, 36, to control the magnitude and timing of the linear gradient pulses imposed along the three axes upon vessel 10 and tissue 12, and to signal generator 54 to control the frequency, magnitude, and timing of the RF pulses.

Processor 70 is also connected via I/O interface 71 to demodulator 58 to receive the real and imaginary components of the demodulated received RF signal.

Processor 70 is further connected to a memory 72 (which stores software to control the operation of the system and data representing the received RF signals), to a CRT 74 (which displays images representing the received RF signal, as well as information needed by the operator to control the system), and to a keyboard 76 (by which the operator can enter data and information to control the entire operation of the system). A camera 75 attached to CRT 74 takes photographs of the displayed images.

Figure 3:
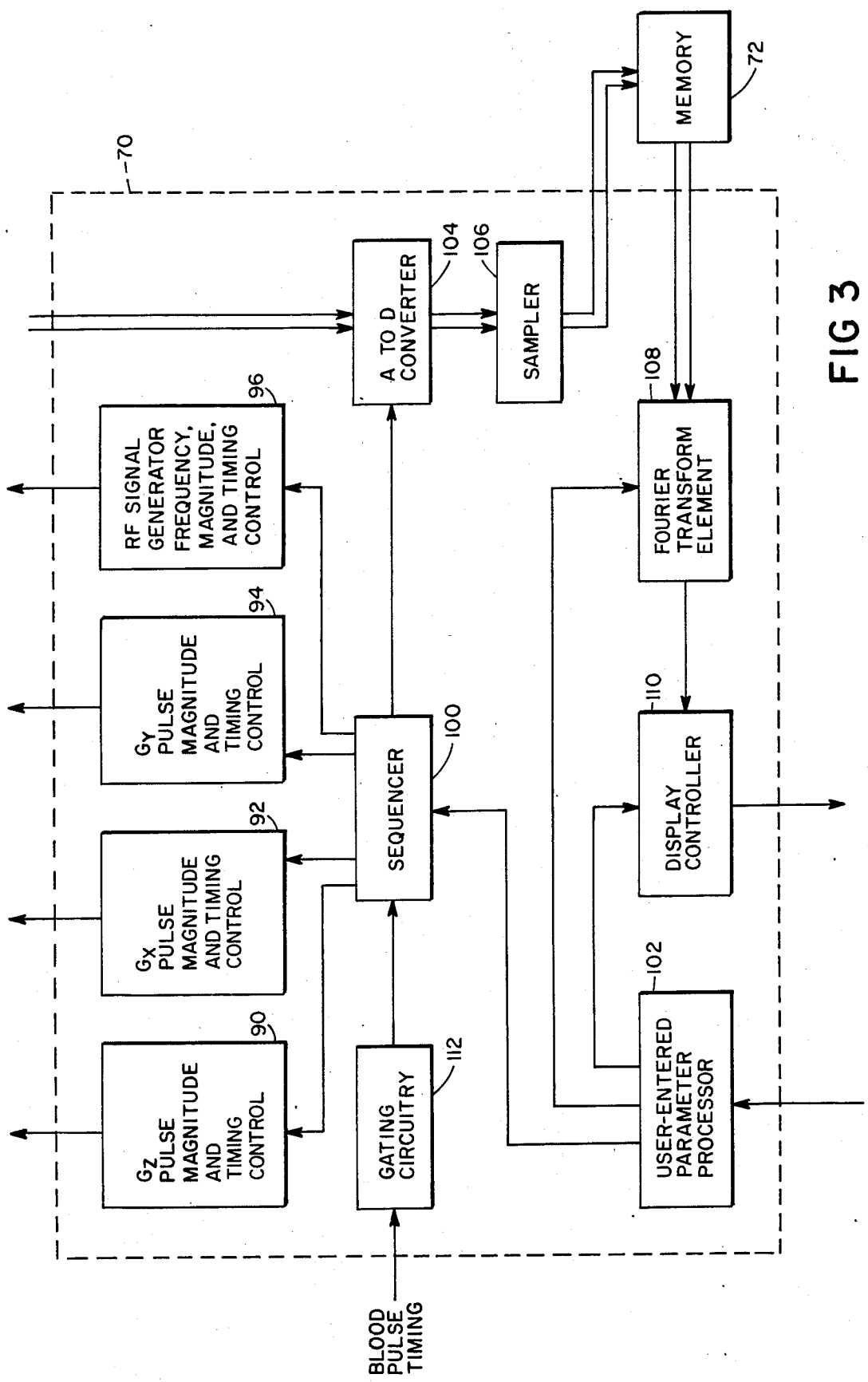
FIG. 3 is a block diagram of portions of the computer processor of FIG. 2.

Referring to FIG. 3, processor 70 includes $G_z$ pulse magnitude and timing control 90 which is connected to trigger $G_z$ driver 36 to apply selected levels of gradient at selected times. Likewise $G_x$ and $G_y$ pulse magnitude and timing controls 92, 94 are connected to trigger respectively $G_x$ and $G_y$ drivers 42, 44.

Similarly RF signal generator frequency, magnitude, and timing control 96 is connected to trigger RF signal generator 54 to provide an RF pulse having a selected frequency and magnitude, at selected times.

Controls 90, 92, 94, 96 are all connected to a sequencer 100 which provides the necessary specific magnitude, timing, and frequency parameters at the proper times for a given NMR field pulse sequence.

Sequencer 100 is connected to a user-entered parameter processor 102 which receives parameters from the keyboard and converts them to a form usable by sequencer 100.

Sequencer 100 is also connected to control an A-to-D converter 104 which is in turn connected to demodulator 58 to digitize the real and imaginary components of the received RF signal. A sampler 106 is connected to the converter 104 to sample the digitized signal components and to memory 72 to store the samples for later processing.

A Fourier transform element 108 is connected to memory 72 for performing a complex two-dimensional Fourier transform on a family of received signal samples to produce real and imaginary components of a two-dimensional array of data in the frequency domain. The parameters in accordance with which the Fourier transform is performed are received from processor 102 based on user entered information.

A display controller 110 is connected to Fourier transform element 108 to organize and process the frequency domain data into image information for delivery to CRT 74, again in accordance with parameters received from processor 102 as provided by the user.

Sequencer 100 is also connected to gating circuitry 112 which provides signals enabling the sequencer to synchronize successive pulse sequences to occur at the same point in successive heart beats.

The invention can be implemented by appropriately configuring available hardware and by specifying operating parameters for available related software, in accordance with the foregoing and following description (for example, NMR imaging hardware and software available from Technicare Corporation, Solon, Ohio, or similar systems available from other vendors).

OPERATION

Figure 4:
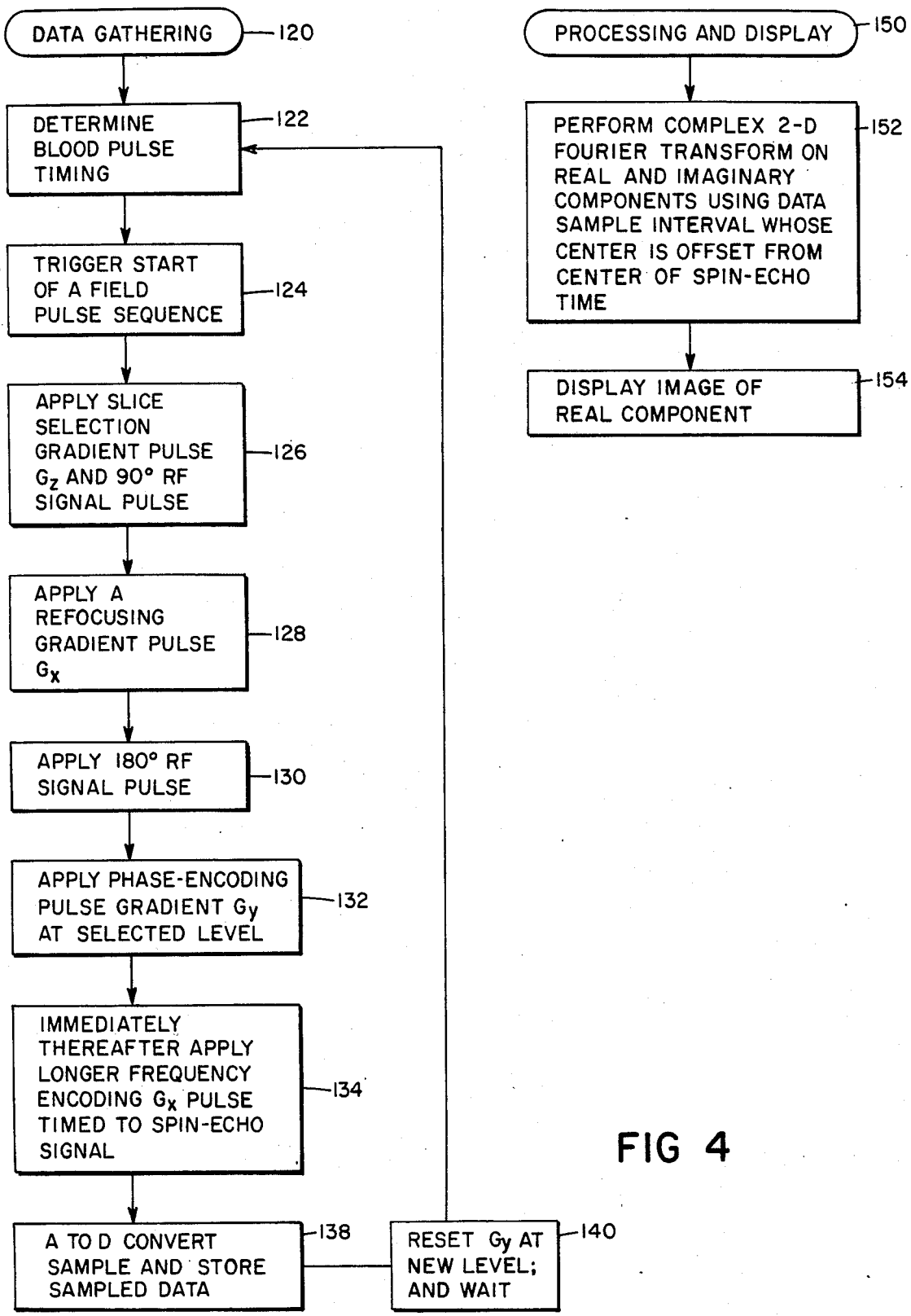
FIG. 4 is a flow chart of data gathering and processing and display steps.
Figure 5:
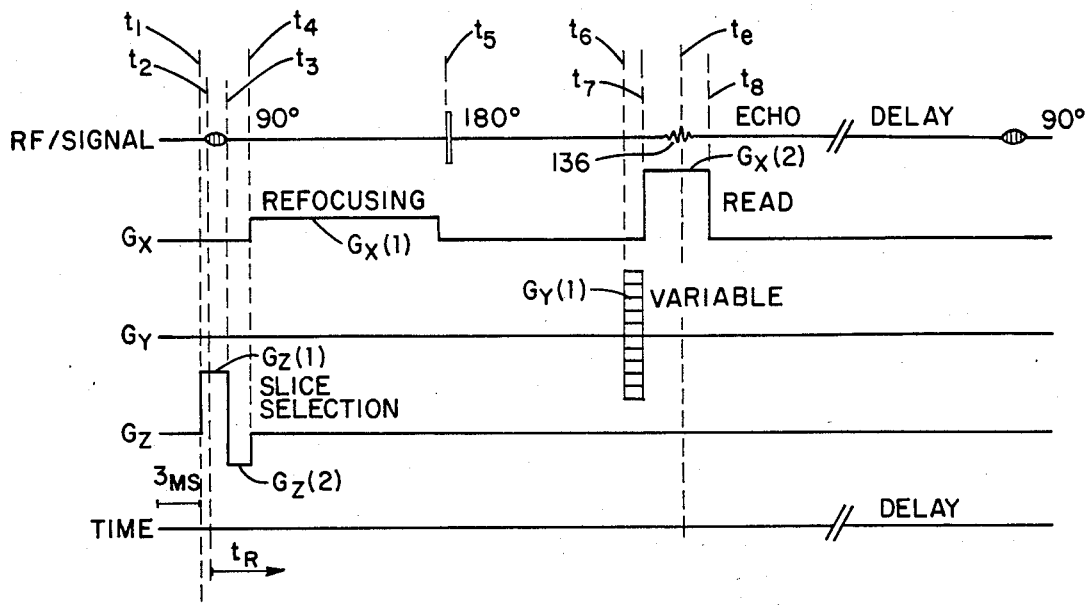
FIG. 5 is a timing chart (not to scale) of a pulse sequence for slice-selective imaging.

Referring to FIGS. 4, 5, in order to generate blood velocity profile images corresponding to planar slice 18 (FIG. 1), vessel 10 is oriented as nearly as possible to lie in the x-y plane with the predominant direction of its axis lying along the x-axis, and the system parameters are configured to perform two series of steps, one for data gathering and the other for processing and display. In the data gathering series (120), the blood pulse timing is first determined (122). At a preselected time ($t_1$) relative to the blood pulse a signal pulse sequence is begun (124) by applying a slice selective field gradient pulse $G_z(1)$ (126). While the slice selective gradient is being applied, a 90° RF pulse is applied during the period between times $t_2$ and $t_3$ (126). The effect of the $G_z$ and RF pulses is to excite only those nuclei within planar slice 18, the slice of interest. During the period between times $t_3$ and $t_4$ a gradient $G_z(2)$ of opposite polarity to $G_z(1)$ is applied. At time $t_4$, a refocusing gradient pulse $G_x(1)$ is applied (128). At time $t_5$, a 180° RF signal pulse is applied (130) to flip the magnetization vector of the nuclei, causing their phases to tend to reconverge.

In the interval between times $t_6$ and $t_7$ a linear phase-encoding pulse gradient $G_y$ at a selected level (e.g., level $G_y(1)$ on FIG. 5) is applied (132) to encode the nuclei along the y-axis with different phases. Immediately thereafter and during the interval between times $t_7$ and $t_8$, a linear frequency-encoding gradient "read" pulse $G_x(2)$ is applied (134) which imparts different frequencies to different nuclei along the x-axis. Pulse $G_x(2)$ is timed to occur over an interval which spans the spin-echo signal 136, whose center point occurs at $t_e$.

The time durations of the $G_x$, $G_y$, and $G_z$ gradient pulses are shown only schematically in FIG. 5. Preferably pulse $G_y$ is about two to three times as long as pulse $G_z$, and pulse $G_x$ is about 5 to 20 times as long as pulse $G_y$. Thus for $G_z$ between 1 and 2 milliseconds, $G_y$ would be between 2 and 3 milliseconds, and $G_x$ between 10 and 20 milliseconds. It can be shown (as suggested in the Hahn article cited above) that the phase shift in a spin echo experiment depends on the square of the time duration of the gradient pulse. The contribution of the x-axis gradient pulse and hence of the velocity component along the x-axis is thus caused to dominate the total phase shift. For example, with $G_x$ lasting 10 times longer than $G_y$, the x-axis velocity will be weighted by a factor of 100 in the phase shift.

Referring again to FIGS. 4, 5, spin-echo signal 136 is sensed, A-to-D converted and sampled, and the samples (representing a time sequence of signal amplitude levels) are stored (138). That completes the data gathering steps for one time dependent set of signal samples. (The identical steps can be repeated several times with the results being averaged to improve the signal-to-noise ratio.)

A family of such signal sample sets is obtained by repeating the steps a number of times, each time using a different magnitude for the phase-encoding gradient pulse $G_y$. Thus, between iterations, the level of $G_y$ is reset and a delay period is allowed to pass (140) before the next iteration begins. The delay period can be selected to synchronize each iteration with the heart beat.

Once the family of signal sample sets are taken and stored, they are processed and displayed (150). A complex two-dimensional Fourier transformation is performed (152) to give spatially dependent real and imaginary components in the frequency domain for a two-dimensional array of pixels, and the real component array is displayed (154) as an image representative of the velocity profile of the blood over planar slice 18. In the image, the intensity represents the real part of the complex image datum at each pixel. The midpoint of the greyscale represents the zero value. Data with real parts greater than zero (corresponding to phase angles with positive cosines) give an image intensity value greater than the zero value. Data with negative real parts give image values less than the zero value.

Figure 6:
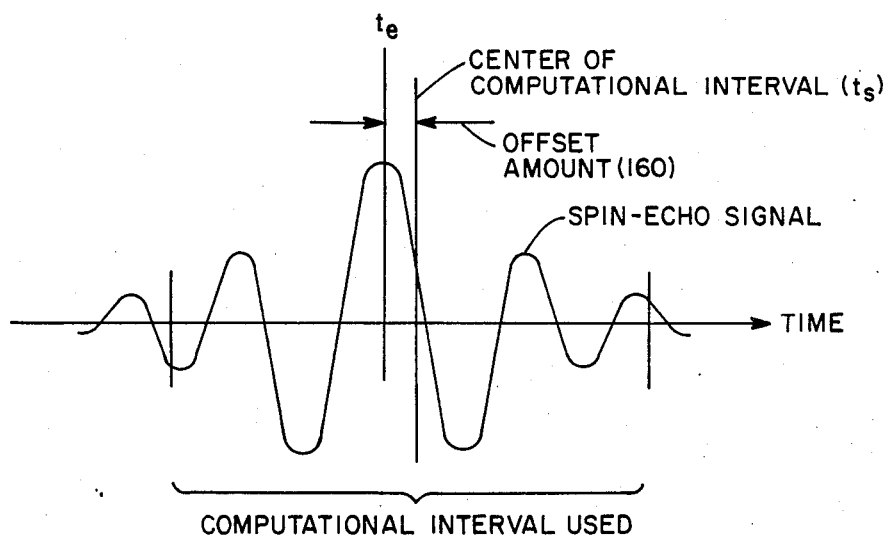
FIG. 6 is a graph of spin-echo signal data.

Referring to FIG. 6, in performing the Fourier transformation, the set of signal samples which are used for the computation span a time interval whose center time ($t_s$) is different by a small offset amount 160 from the center of the spin-echo signal ($t_e$). The effect of the offset in the Fourier transformation process is that the image data is multiplied by a phase factor that depends linearly on the frequency-encoded coordinate, x. For each sampling interval (e.g., 30 microseconds) within the offset amount there is produced 180° of total background phase variation across the image in the x direction. The result is a striping of the image which improves readability.

Information about the motion of the blood through vessel 10 during the course of each pulse sequence can be shown to be carried through to the Fourier transformed spatially dependent data in the form of apparent phase shifts, whose magnitudes depend on the velocities of the nuclei. The real component of the Fourier transformed data preserves this phase shift information, so that a display of the real component will show variations in the phase shift in a pattern which will reflect the velocity profile within vessel 10. By orienting the length of the blood vessel along the same axis (the x-axis) as the frequency encoding gradient pulse, and by making the frequency encoding gradient pulse longer than the phase encoding pulse, the resulting Fourier transformed image data is made more sensitive to velocity along the x-axis than along the y-axis. Offsetting the sample interval relative to the center of the spin-echo signal has the effect of adding a linearly increasing phase shift in the x-axis direction which produces a highly useful striping of the image as explained below. Placing the phase-encoding pulse $G_y$ close in time to the frequency-encoding pulse $G_x$ reduces any error which might occur as a result of the nuclei changing position between the two pulses.

In one example, a velocity profile image was formed of water flowing through a 7/16" inside diameter tube. Flow was constant, gravity driven, and calibrated with a Mettler top-loading scale. The water was doped with $CuSO_4$ to have a relaxation constant $T_1$ of approximately 300 milliseconds at 20 megaherz. The tube was placed in the magnetic field with its axis aligned with the direction of the frequency-encoding gradient (i.e., along the x-axis). Because the flow was constant, rather than pulsatile, the pulse sequences were not gated to flow pulses, but were simply repeated every 300 milliseconds. The frequency encoding gradient strength was $6 \times 10^3$ Hz/cm. The resulting phase shift as a function of velocity of the nuclei can be calculated as 8.2 radians/cm/sec. The ratio depends on the pulse sequence which is preferably arranged so that the ratio will produce an image with striping which is useful for the flow velocities of interest. Ratios of at least 0.2 radians/cm/sec. appear to be useful. The magnet was a 1.44 T. (61.5 MHz) 8 cm superconducting magnet (fabricated by Technicare, Solon, Ohio).

Figure 7:
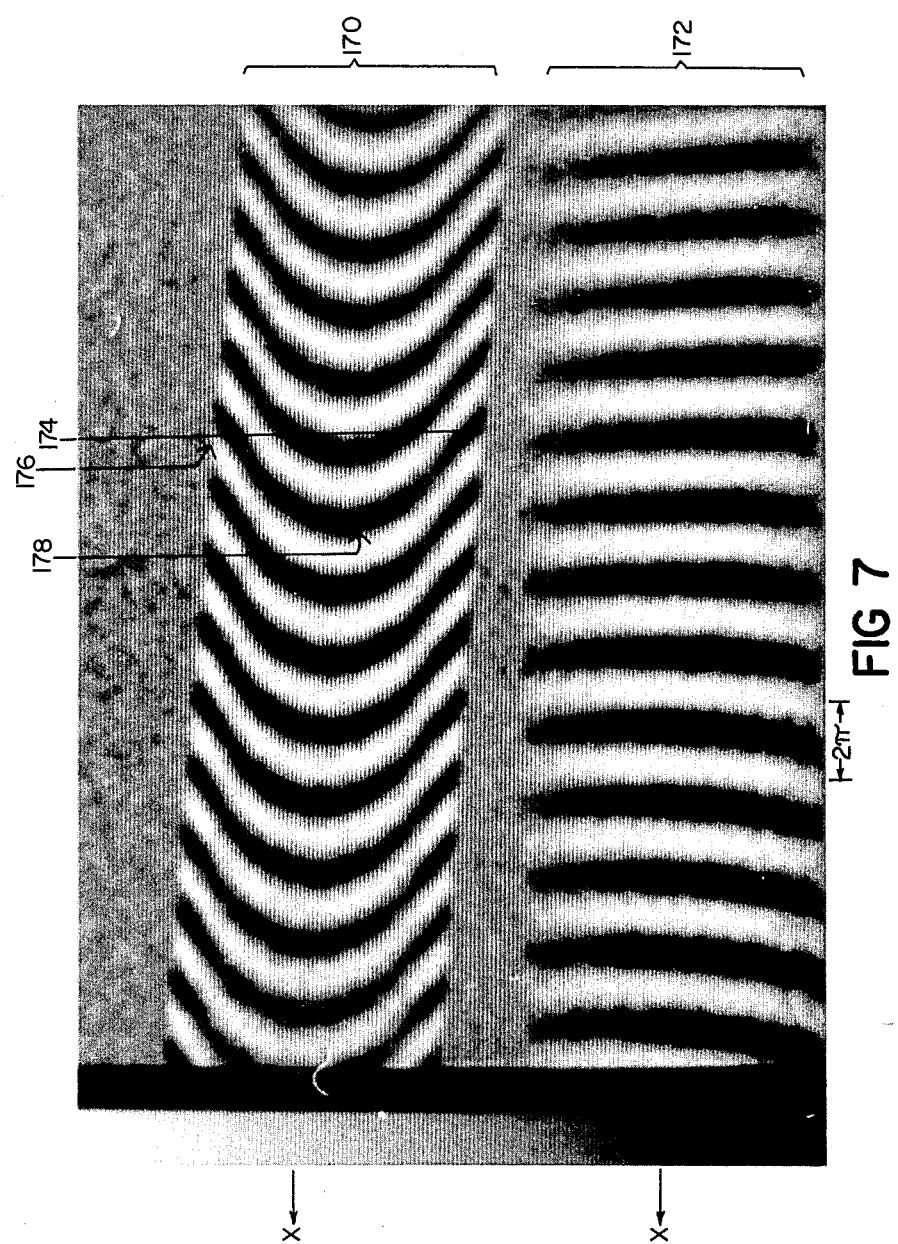
FIG. 7 is an image of two parallel tubes respectively containing static fluid and moving fluid.

Referring to FIG. 7, the upper half 170 is a display of the real component of the Fourier transformed data resulting from fluid flow in the tube, while the lower half 172 resulted from an identical tube with the fluid not flowing.

The lower half image 172 shows a stripe pattern with the stripes orthogonal to the x-axis. The stripes represent a background phase which increases linearly with distances along the x-axis. Each black or white stripe represents a background phase shift of 180° ($\pi$ radians). In upper half image 170, the phase shift due to the motion of the fluid is superimposed over the linear background phase shift. Thus the image gives an easily seen representation that the velocity along the central axis of the tube is higher than along the wall (because at the central axis the phase shift per unit length along the x-axis is greater). Further, because each stripe represents 180° of phase shift, it is possible to measure the difference between the phases at the wall and at the central axis at one position (174) along the x-axis by counting the number of stripes which must be traversed along the central x-axis in order to reach the stripe which begins at line 174 at the wall of the tube. Here there are 3 stripes between points 176, 178, which amounts to a $3\pi$ radians phase shift which translates to a maximum flow velocity of 1.2 cm/sec $$\frac{(3\pi \text{ radians} = 1.2 \text{ cm/sec})}{8.2 \text{ radians/cm/sec}}$$

or an average flow velocity of 0.6 cm/sec, which is within 15% of the mechanically calibrated average velocity.

The display format enables direct inference from striping of data phase with a precision of +90°, which is acceptable if small compared with typical phase shifts being studied. By using pulse sequences whose magnitude and duration produce relatively high phase shift/velocity ratios, phase shifts of many times 360° can be obtained.

Figure 8A:
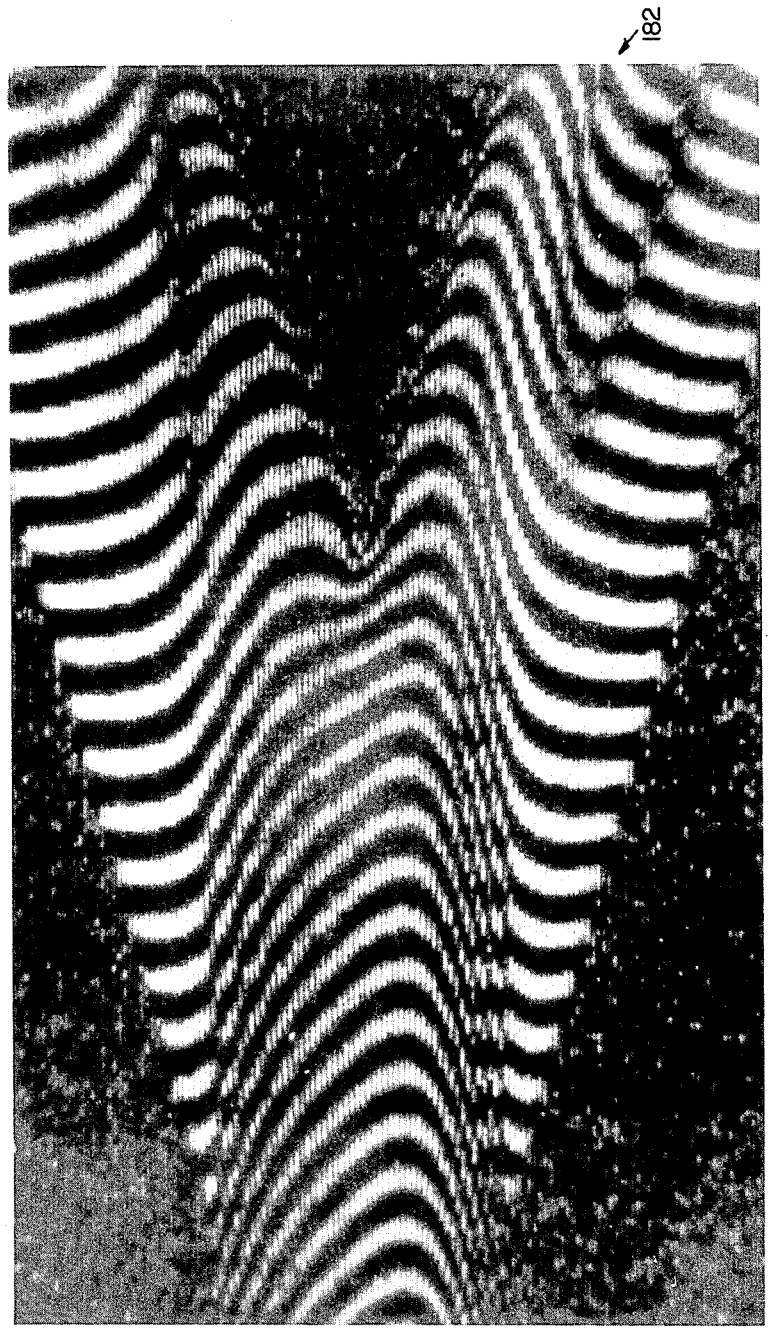
FIGS. 8A to 8C show images of bifurcating tubes respectively containing moving fluid and static fluid, and recombining tubes containing moving fluid.
Figure 8B:
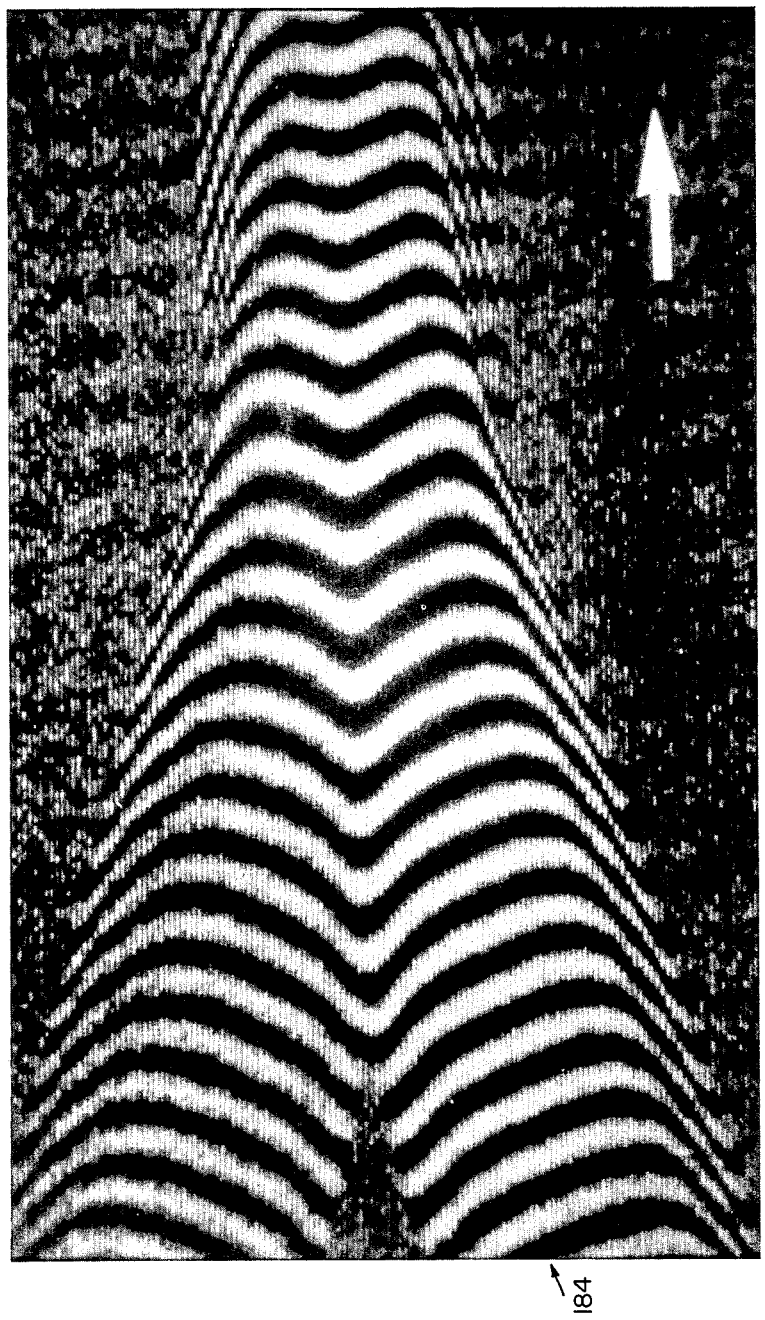
Figure 8C:
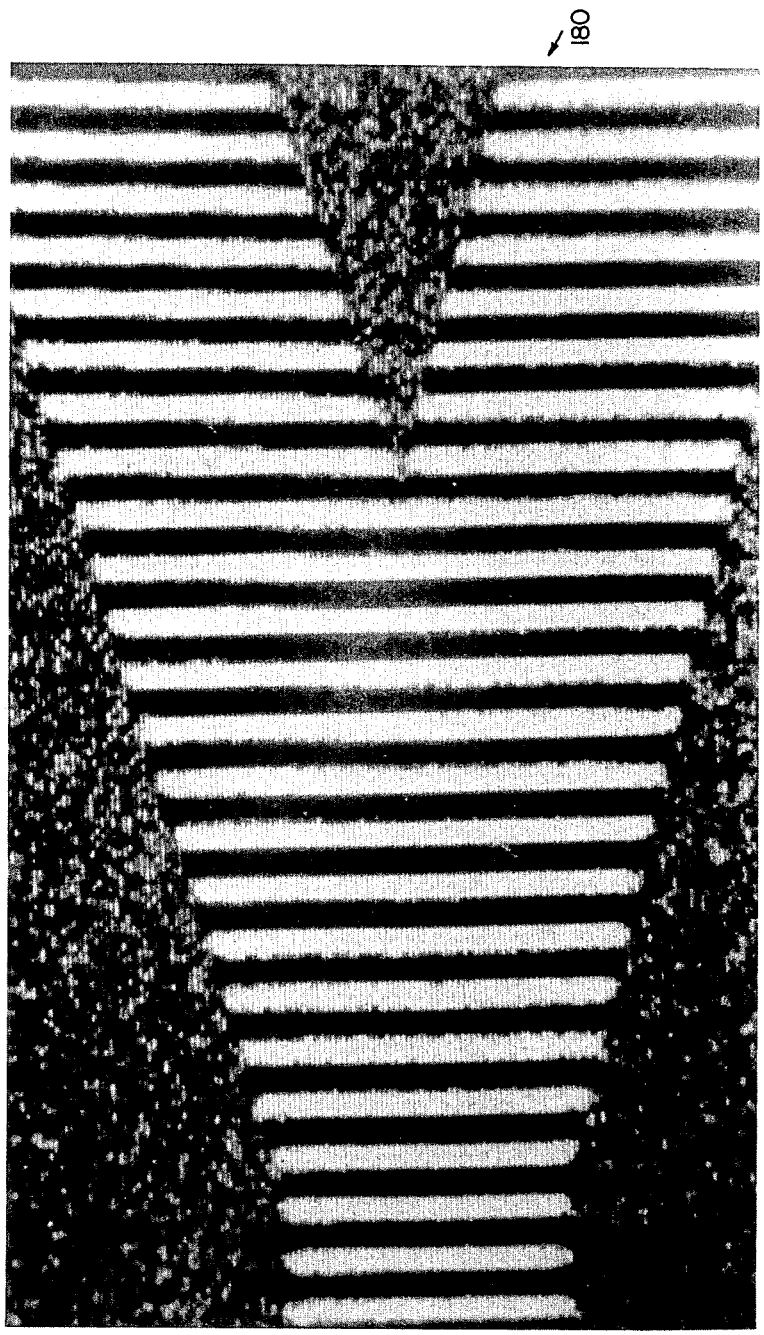

Referring to FIG. 8, in another example, the phase image produced by non-moving fluid in a bifurcating tube is shown in the lower left (180), and produces a set of parallel stripes representing the background phase offset. When the fluid is moving (182), the stripe pattern is shifted to reflect the velocity profile of the fluid. An image of fluid moving through tubes which recombine is shown in the upper right of FIG. 8 (184). In FIG. 8, the tube diameter is $\frac{1}{2}$", and flow rate is 100 cc/min. The maximum phase shift discernible on the images is $10\pi$ radians corresponding to a maximum velocity of 3.83 cm/sec. The maximum expect velocity (based on fluid mechanics) is 4.0 cm/sec., within about 2% of the measured figure.

Figure 9A:
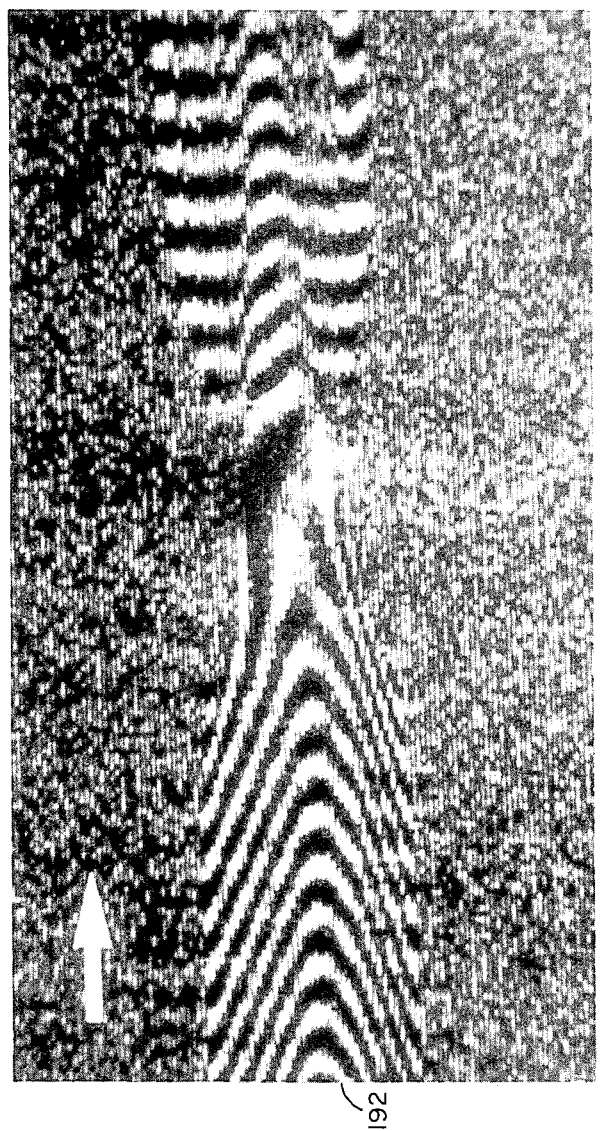
FIGS. 9A and 9B show images of constricted tubes respectively containing moving fluid and static fluid.
Figure 9B:
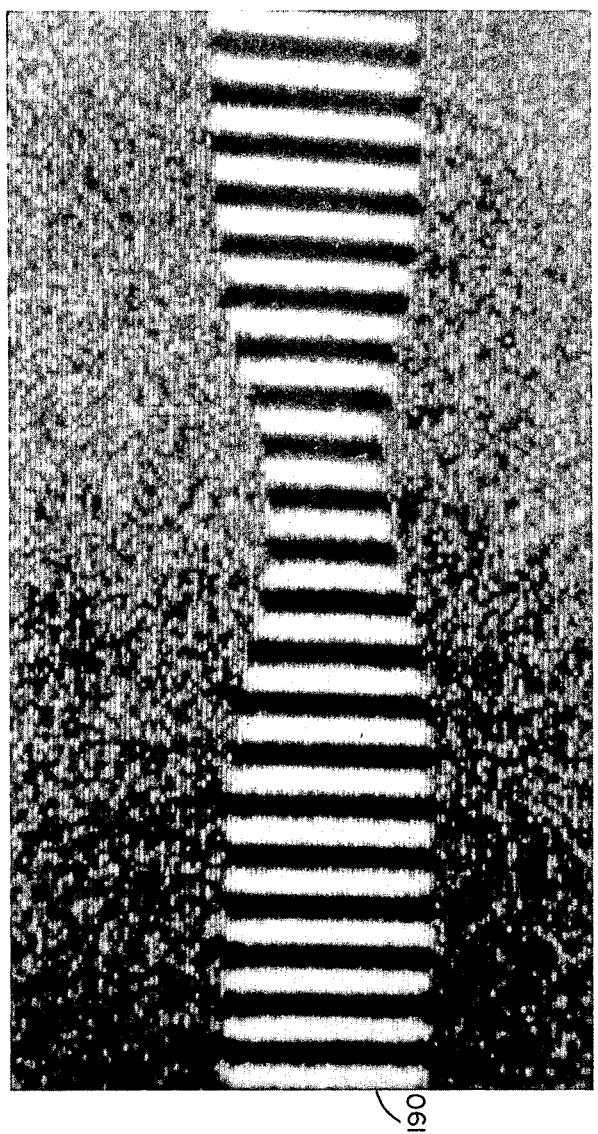

Referring to FIG. 9 in another example, images of a 3/16" inside diameter tube with a 3/32 inch stenosis (constriction) are shown for non-moving (190) and moving fluid (192).

In the images of moving fluid, velocity is inferred from the displacement of the stripes left or right, with the slopes of the stripes representing changes in flow velocity. Phase stripes which show forward concavity thus do not imply retrograde flow, but rather the existence of higher shear rates near the central axis compared with the tube wall (as in laminar flow).

Pixels where the phase becomes indistinct correspond to points where the velocity gradient is high enough that different velocity values coexist within one pixel. Interference of the resulting phases causes loss of signal, an effect which can be reduced by increasing the spatial resolution.

Introduction of a background phase offset into the imaging phase enhances the readability of phase shifts for four reasons. First, phase shifts can be calculated in two ways: stripe count or X displacement. Accuracy and precision are improved by this redundancy. Second, two-dimensional Fourier transform images have better resolution in X than in Y which gives the X displacement method the advantage. Third, background offset exposes any imperfections in the background phase, enabling correction by the reader. Fourth, in consequence of the first three advantages, phase offset enables the implementation of pulse sequences with higher characteristic velocity/phase shift ratios, reducing the importance of any residual phase ambiguity.

The system can also be used to generate so-called projection images, in which data from a number of stacked planar slices are effectively accumulated into one array. For example, a projection image of FIG. 1 would represent not only slice 18 but slices above and below it along the z-axis.

Figure 10:
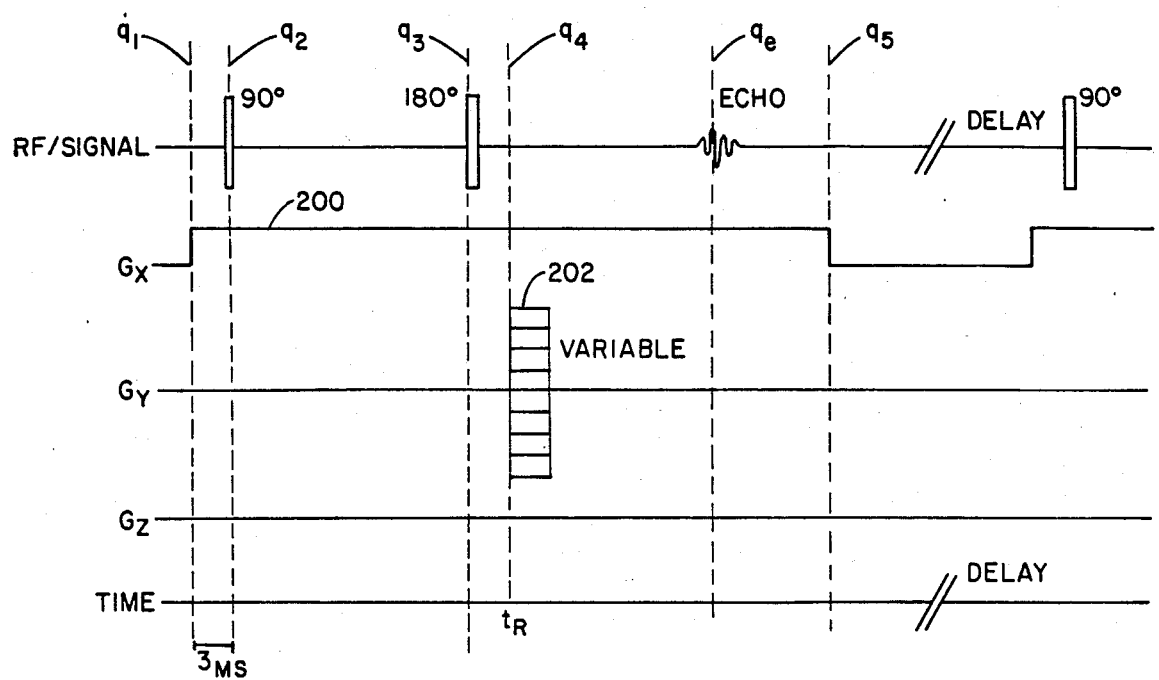
FIG. 10 is a timing chart of a pulse sequence for projection imaging.

Referring to FIG. 10, the pulse sequence for taking a set of samples for a projection image begins a time $q_1$ with the start of a long frequency-encoding gradient pulse 200. No slice-selective gradient pulse $G_z$ is used since the image is not meant to be slice-selective. At time $q_2$ (while the $G_x$ pulse continues) a 90° RF pulse is imposed, followed by a 180° pulse at time $q_3$, and a phase encoding gradient pulse 202 beginning at time $q_4$. The spin-echo signal is centered at time $q_e$. Gradient pulse 200 ends at time $q_5$, after which a delay occurs before the next pulse sequence begins. Thus, the projection images are obtained without either slice selection or z-axis encoding.

The Fourier transformation of the sets of data samples is performed without imposing the background phase offset used for the slice-selective images. Instead, the data component 90° away from the phase of the stationary nuclei in the object being imaged is the one used to form the image. This in effect suppresses the contribution of the stationary nuclei to the final image, while emphasizing the contribution of the moving nuclei. A greater than 90% reduction in stationary nuclei signal intensity has been achieved, permitting the imaging of flow velocities greater than 10 cm/sec with vessel diameter to total diameter ratios greater than 1/20.

Figure 11A:
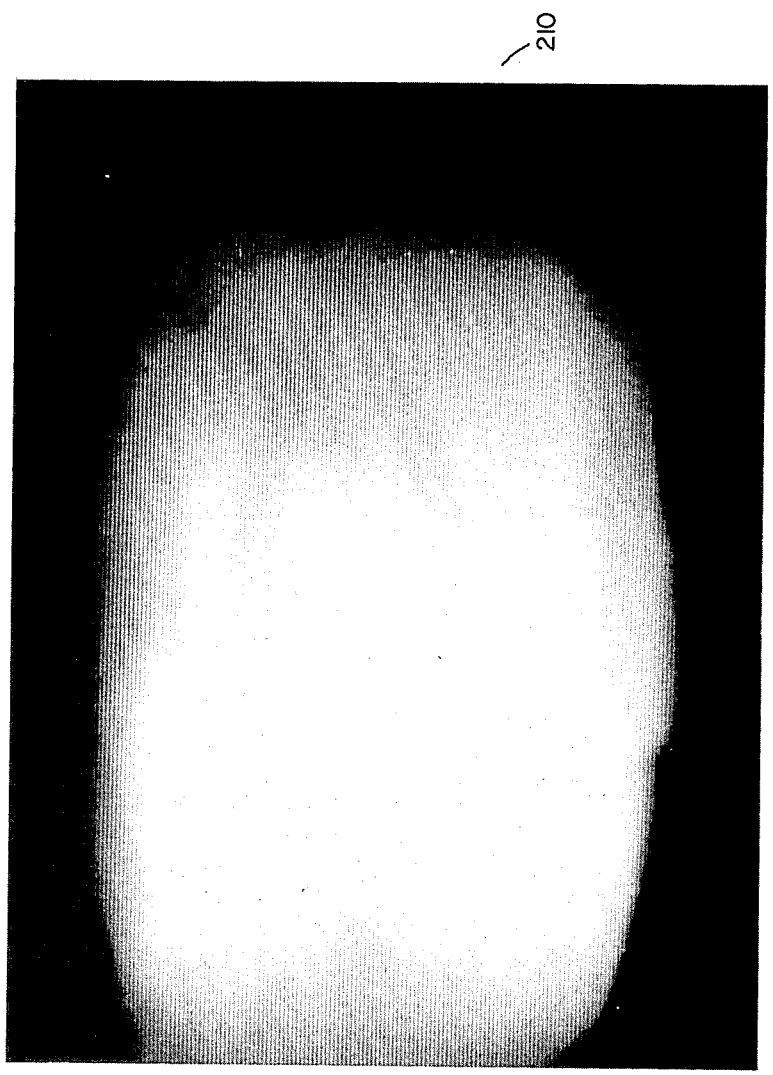
FIGS. 11A and 11B show projection images of a bifurcating tube which contains moving fluid and is immersed in a container of water.
Figure 11B:
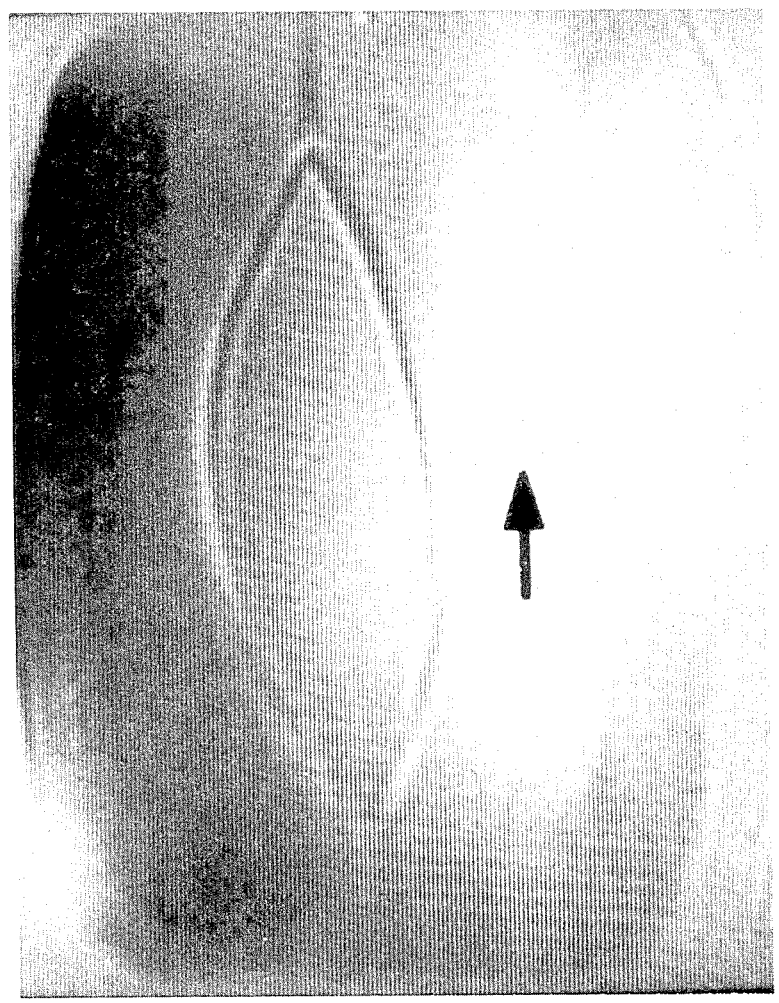

Referring to FIG. 11, the upper portion 210 shows a projection image of a bifurcating and recombining tube through which fluid is flowing at 300 cc/min. The $\frac{1}{4}$" inside diameter tubing lies within an 8"×10"×12" cavity of stationary water. The measured maximum phase shift is $5\pi$ radians which implies a maximum velocity of $V_{max}=6.44$ cm/sec. The expected value of $V_{max}$ is 12.0 cm/sec, illustrating that projection imaging underestimates velocities. In this case, however, it would be more reasonable to expect projection images to represent the average velocity, $V_{avg}$, rather than $V_{max}$ since the entire tube diameter contributes to the observed phase shift. In this experiment $V_{avg}=6.0$ cm/sec, close to the observed velocity value.

Figure 12:
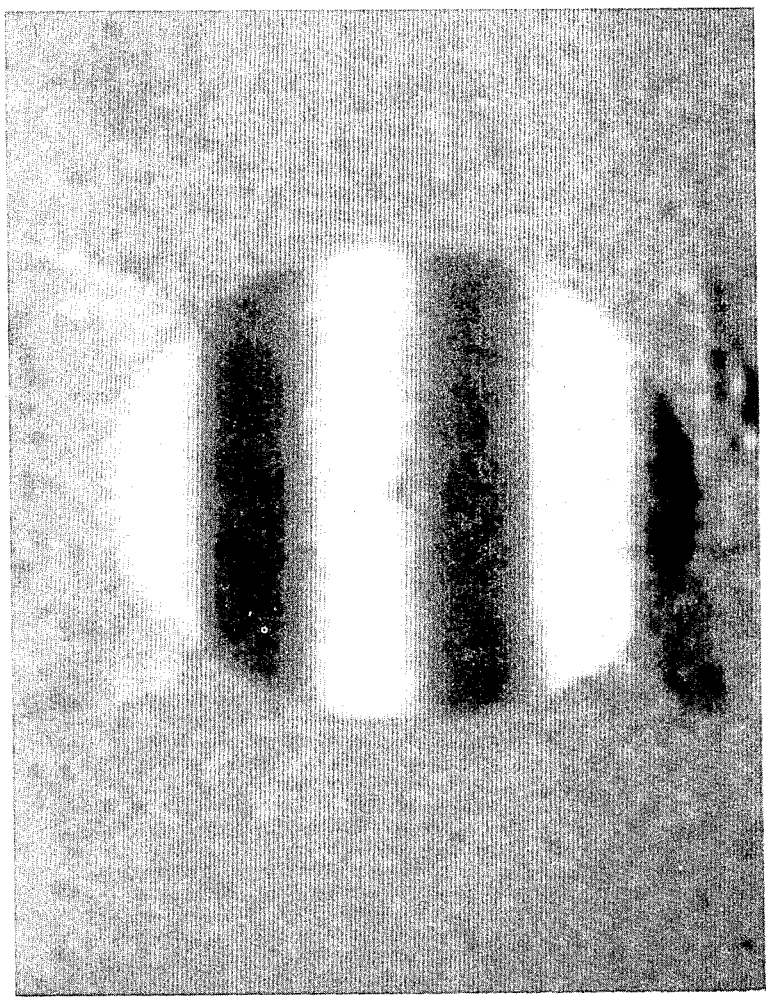
FIG. 12 shows a projection image of a rotating disk.

FIG. 12 is another example of projection imaging, this time of a rotating disc, with the axis of rotation aligned with the z-axis. The disc is composed of water-saturated towels inside a plastic container 20 cm in diameter and 1.5 cm thick. The disk is rotating at 30 rpm corresponding to a maximum tangential velocity of $10\pi$ cm/sec. A rigid body rotating in the x-y plane at frequency w has the property that at any point (x,y), the velocity $V(x,y)=2\pi/w/(y,-x)$. Therefore the x velocity component is proportional to y, and points of equal phase shift lie on horizontal lines (constant y) because they sustain equal x velocities. The pulse sequence was repeated every 300 msec, $t_e=10.0$ msec, the frequency encoding gradient was $G_x=3\times 10^3$ Hz/cm and the calculated ratio of phase to velocity was $P(t_e)/V_x=0.28$ radians/cm/sec. At 30 cm/sec, this corresponds to a total phase shift of $3\pi$ radians which is in reasonable accord with the experiment. This demonstrates that high velocity can yield good signal intensity without spatial distortion.

Projection imaging is highly efficient, enabling three-dimensional volume to be surveyed in times characteristic of two-dimensional imaging experiments.

Other embodiments are within the following claims.

We claim:

1. Nuclear magnetic resonance apparatus for forming an image representative of a velocity profile of a fluid flowing in a vessel comprising
    means for stimulating the fluid to produce a time-dependent magnetic resonance signal,
    means for producing Fourier-transformed data from said time-dependent magnetic resonance signal,
    said means for stimulating including means for introducing into a predetermined component of said Fourier-transformed data, spatially dependent phase information indicative of said velocity profile of said fluid, and
    means for extracting said predetermined component of said Fourier-transformed data for display as said image representative of said velocity profile.

2. The apparatus of claim 1 wherein
    said phase information includes phase values for an array of positions in said fluid,
    said image comprises an array of display points each characterized by a visual parameter whose magnitude represents said phase value for a corresponding position in said fluid, and
    said means for producing said Fourier-transformed data includes means for imposing, on said phase values, phase offset amounts to impart a visible pattern to the velocity information represented in said image.

3. The apparatus of claim 2 wherein said phase offset amounts increase linearly with distance along a predetermined direction in said fluid, and
    said visible pattern is a set of stripes spaced along one dimension of said image corresponding to said predetermined direction.

4. The apparatus of claim 3 wherein
    in the absence of flow, said stripes are parallel, evenly spaced along and perpendicular to said dimension.

5. The apparatus of claim 3 wherein
    for fluid flowing with different velocities at different positions, the velocity profile is represented by the contours and locations of said stripes on said image.

6. The apparatus of claim 3 wherein the distance between opposite edges of one said stripe represents a phase difference of 180°.

7. The apparatus of claim 2 wherein said means for producing Fourier-transformed data includes
    means for calculating a Fourier transformation from a selected time segment of said time-dependent resonance signal, and
    means for selecting the beginning and end of said time segment to produce said phase offset amounts.

8. The apparatus of claim 7 wherein said
    means for stimulating includes means for causing a spin-echo signal having a center time point of maximum magnitude, and
    said time segment is selected to be off-center by an offset value with respect to said center time point of said spin-echo signal.

9. The apparatus of claim 8 wherein said visible pattern depends on the size of said offset value.

10. The apparatus of claim 3 wherein said vessel is arranged with the predominant direction of flow of said fluid aligned with said predetermined direction.

11. The apparatus of claim 2 wherein said visual parameter is intensity of the image.

12. The apparatus of claim 1 wherein said means for stimulating includes
    means for imposing on said vessel a first magnetic gradient pulse along one direction for introducing phase information indicative of velocity of said fluid along said one direction, and a second magnetic gradient pulse along a second direction, and
    means for regulating the durations of said pulses so that said first magnetic gradient pulse is longer than said second magnetic gradient pulse to cause velocity of said fluid along said one direction to have greater influence on said image than velocity of said fluid along said second direction.

13. The apparatus of claim 12 wherein said one direction and said second direction are perpendicular to one another.

14. The apparatus of claim 12 wherein said first magnetic gradient pulse is at least five times longer than said second magnetic gradient pulse.

15. The apparatus of claim 12 further comprising
    means for orienting said vessel with the predominant direction of flow aligned with said one direction.

16. The apparatus of claim 1 wherein said means for stimulating includes
    means for imposing on said vessel a first magnetic gradient pulse along one direction for introducing phase information indicative of velocity of said fluid along said one direction, and a second magnetic gradient pulse along a second direction, and
    means for regulating the timing of the occurrence of said pulses to reduce the effect on said image of velocity of said fluid along said second direction.

17. The apparatus of claim 16 wherein said first pulse is imposed immediately after said second pulse.

18. The apparatus of claim 1 wherein
    said means for producing Fourier-transformed data includes means for phase-sensitive detection of real and imaginary components of said time-dependent magnetic resonance signal, and said predetermined component is the real component of said Fourier-transformed data.

19. The apparatus of claim 1 wherein said means for stimulating includes means for imposing magnetic pulses of a magnitude and timing to produce a selected ratio between velocity of said fluid along one direction and corresponding phase values within said phase information.

20. The apparatus of claim 19 wherein said ratio is selected on the basis of the predominant velocity of interest of said fluid.

21. The apparatus of claim 20 wherein said ratio is at least 0.2 radians per centimeter per second.

22. The apparatus of claim 1 arranged for producing a projection image representative of said velocity profile and wherein
said vessel comprises part of a larger specimen,
said specimen includes stationary portions,
said Fourier-transformed data includes a component which carrier phase information derived from said stationary portions, and
said means for extracting includes means for deriving a component from said Fourier-transformed data which reduces the effect of said stationary portions on said image.

23. The apparatus of claim 22 wherein said component derived by said means for deriving is 90° out of phase from said component which carries said phase information from said stationary portions.

24. The apparatus of claim 1 wherein
said fluid has a predominant direction of flow in said vessel,
said means for stimulating introduces phase information indicative of said velocity profile for velocities along a particular direction, and
said means for stimulating includes means for orienting said vessel with said predominant direction of flow aligned with said particular direction.

25. The apparatus of claim 1 wherein said Fourier-transformed data is produced by means of a complex two-dimensional Fourier transformation.

26. The apparatus of claim 1 wherein said means for stimulating includes means for imposing RF pulses on said vessel, said time-dependent magnetic resonance signals being spin-echo signals resulting from said RF pulses.

27. The apparatus of claim 1 wherein said means for stimulating includes
means for imposing on said vessel a first gradient pulse along an axis (y),
means for imposing on said vessel a second gradient pulse along an axis (x) orthogonal to said y-axis, and
said Fourier-transformed data includes a two-dimensional array of data points, and
said image is two-dimensional.

28. The apparatus of claim 27 wherein said first pulse is a frequency-encoding pulse and said second pulse is a phase-encoding pulse.

29. The apparatus of claim 27 wherein said means for stimulating further includes means for imposing on said vessel a slice-selecting magnetic field gradient pulse, along an axis (z) orthogonal to said x-and y-axes, and
wherein said image corresponds to the velocity profile in a slice through said vessel, said slice being in the x-y plane and at a location along the z-axis based upon said slice-selecting magnetic field gradient pulse.

30. The apparatus of claim 1 wherein
said means for stimulating includes
means for imposing on said vessel a frequency-encoding gradient pulse along a y-axis,
means for imposing on said vessel a phase-encoding gradient pulse along an x-axis orthogonal to said y-axis,
said frequency-encoding gradient pulse being longer than, and occurring immediately after, said phase-encoding pulse, and
means for imposing RF pulses on said vessel to produce, as said time-dependent magnetic resonance signal, a spin-echo signal,
said phase information includes phase values for an array of positions in said fluid,
said image comprises an array of display points each characterized by a visual parameter whose magnitude represents said phase value for a corresponding position in said fluid, and
said means for producing Fourier-transformed data includes
means for phase-sensitive detection of real and imaginary components of said spin-echo signal, and
means for imposing on said phase values phase offset amounts which increase linearly with distance along said x-axis to impart in said image a visible pattern of stripes spaced along one dimension of said image to enhance the velocity information presented in said image.

31. A method for using nuclear magnetic resonance to form an image representative of a velocity profile of a fluid flowing in a vessel comprising
stimulating the fluid to produce a time-dependent magnetic resonance signal,
producing Fourier-transformed data from said time-dependent magnetic resonance signal,
introducing into a predetermined component of said Fourier-transformed data, spatially dependent phase information indicative of said velocity profile of said fluid, and
extracting said predetermined component of said Fourier-transformed data for display as said image representative of said velocity profile.

32. The method of claim 31 further comprising
imposing on said phase information phase offset amounts to impart in said image a visible pattern related to velocity information in said image.

* * * * *